United States Patent
Shibutani et al.

(10) Patent No.: US 8,361,454 B2
(45) Date of Patent: Jan. 29, 2013

(54) PVA PARTICLE FOR TEMPORARY EMBOLIC MATERIAL AND PRODUCTION PROCESS THEREOF, AND TEMPORARY EMBOLIC MATERIAL

(75) Inventors: Mitsuo Shibutani, Osaka (JP); Shinya Wakimoto, Osaka (JP); Yuzo Shomura, Moriguchi (JP)

(73) Assignee: The Nippon Synthetic Chemical Industry Co., Ltd., Osaka (JP)

( * ) Notice: Subject to any disclaimer, the term of this patent is extended or adjusted under 35 U.S.C. 154(b) by 1051 days.

(21) Appl. No.: 11/993,072

(22) PCT Filed: Jun. 28, 2006

(86) PCT No.: PCT/JP2006/312875
§ 371 (c)(1),
(2), (4) Date: Dec. 19, 2007

(87) PCT Pub. No.: WO2007/004484
PCT Pub. Date: Jan. 11, 2007

(65) Prior Publication Data
US 2010/0215613 A1     Aug. 26, 2010

(30) Foreign Application Priority Data

Jul. 1, 2005 (JP) ................................ 2005-194130

(51) Int. Cl.
*A61K 31/74* (2006.01)
*A61K 31/765* (2006.01)
*A61K 9/14* (2006.01)
*A61K 9/00* (2006.01)
*A61K 49/04* (2006.01)

(52) U.S. Cl. ........ 424/78.18; 424/9.1; 424/9.4; 424/489

(58) Field of Classification Search ................ None
See application file for complete search history.

(56) References Cited

U.S. PATENT DOCUMENTS

| 5,034,324 | A | * | 7/1991 | Shinozaki et al. | ............ | 435/178 |
| 2001/0036451 | A1 | * | 11/2001 | Goupil et al. | ............... | 424/78.38 |
| 2003/0206864 | A1 | * | 11/2003 | Mangin | ......................... | 424/9.52 |
| 2004/0096662 | A1 | * | 5/2004 | Lanphere et al. | ............. | 428/402 |

FOREIGN PATENT DOCUMENTS

| JP | 56-120707 | | 9/1981 |
| JP | 8-188619 | A | 7/1996 |
| JP | 2000-265026 | A | 9/2000 |
| JP | 2002-527206 | A | 8/2002 |
| JP | 2004-167229 | A | 6/2004 |
| JP | 2005-89606 | A | 4/2005 |
| WO | WO 98/03203 | | 1/1998 |
| WO | WO99/12577 | A1 | 3/1999 |
| WO | WO 03/084582 | A1 | 10/2003 |

OTHER PUBLICATIONS

Hanway Company. http://www.hanwaycompany.com/pvaen.htm. Accessed Mar. 11 2011. No date. 4 printed pages.*
Ty Ting, I Gonda, EM Gipps. "Microparticles of Polyvinyl Alcohol for Nasal Delivery. I. Generation by Spray-Drying and Spray-Desolvation." Pharmaceutical Research, vol. 9 No. 10, 1992, pp. 1330-1335.*
L Pereswetoff-Morath. "Microspheres as Nasal Drug Delivery Systems." Advanced Drug Delivery Reviews, vol. 29, 1998, pp. 185-194.*
Chang Chun Chemical Corporation. "PVA Polyvinyl Alcohol." Downloaded May 14, 2012. pp. 1-45, plus two front cover pages and one back cover page.*
International Preliminary Report on Patentability; International Application No. PCT/JP2006/312875; International Filing Date: Jun. 28, 2006.
Written Opinion; International Application No. PCT/JP2006/312875; International Filing Date: Jun. 28, 2006.
International Search Report; International Application No. PCT/JP2006/312875; Date of mailing of the international search report: Sep. 12, 2006.
Extended European Search Report; dated Dec. 12, 2011 of European Patent Application No. 06 767 492.9.
Sisken et al: "Pathologic Evaluation of a Spherical Polyvinyl Alcohol Embolic Agent in a Porcine Renal Model", Journal of Vascular and Interventional Radiology, VA, vol. 14, No. 1, Jan. 1, 2003, pp. 89-98.
Mark H F et al., "Vinyl alcohol polymers", Jan. 1, 1989, Encyclopedia of Polymer Science and Engineering, John Wiley & Sons, New York, pp. 181-186.

* cited by examiner

*Primary Examiner* — Frederick Krass
*Assistant Examiner* — Isaac Shomer
(74) *Attorney, Agent, or Firm* — Antonelli, Terry, Stout & Kraus, LLP.

(57) ABSTRACT

A temporary embolic material for blood vessel which can embolize a blood vessel in a living body and is used for the temporary embolization of the blood stream. More specifically, disclosed is an embolus-forming material comprising a specific PVA particle which can be used for the closure of the inner lumen of a blood vessel by the PVA particle to embolize the blood stream, which can ultimately be absorbed in the living body, which can be excreted out of the body and which does not remain in the body. A pearl-like polyvinyl alcohol particle for use as a temporary embolic material, the particle having a saponification degree of 90 mol % or higher and an average particle diameter of 70 to 1000 μm; and a temporary embolic material comprising the particle mixed or dissolved therein.

7 Claims, No Drawings

PVA PARTICLE FOR TEMPORARY EMBOLIC MATERIAL AND PRODUCTION PROCESS THEREOF, AND TEMPORARY EMBOLIC MATERIAL

RELATED APPLICATION

This is a U.S. national phase application under 35 U.S.C. §371 of International Application No. PCT/JP2006/312875 filed Jun. 28, 2006, which claims priority of Japanese Application No. 2005-194130 filed on Jul. 1, 2005.

TECHNICAL FIELD

The present invention relates to a blood vessel embolic material for temporarily embolizing a blood vessel in a living body and used for temporarily blocking blood flow.

BACKGROUND ART

There has been known an arterial embolization technique for blocking nutrition by vascular blockage for malignant tumors and uterine fibroids incapable of removing surgically, in advance of incision in a surgical operation, in addition to purposes such as minimization of bleeding and hemorrhage prevention. Further, there has been known a chemical embolization process that blocks blood flow in a malignant tumor and expects the improvement of an anti-malignant tumor effect by keeping the concentration of an anti-malignant tumor medicine at a high level, by administrating the anti-malignant tumor medicine in combination with a blood vessel embolic material. As these embolic materials injected in the blood vessel, formulated particles of EVOH (DMSO solution with concentration of about 10%), cyano acrylate and polyvinyl alcohol (PVA) are known.

These embolic materials, for example, EVOH (a DMSO solution with a concentration of about 10%) has bad influences on the living body because the solvent DMSO solvent has toxicity. Cyano acrylate can control an embolization time in the blood by adjusting a mixing ratio with a hydrolyzed product of iodized fatty acid ester but the balance of the mixing ratio is difficult and when timing for extracting a catheter is mistaken after administration in the blood vessel through the catheter, the edge of the catheter adheres in the blood vessel and in the worst case, there is a fear that the edge of the catheter remains in the blood vessel. Further, the formulated particle of PVA is a permanent embolization material and there is a problem that it cannot be used for a temporary embolization use.

Various studies have been carried out for solving these problems. For example, in International Publication No. WO 98/03203, a gelatin sponge is used for temporary embolization, however, since a component derived from an organism is contained in the gelatin sponge, there is a fear that it mediates infection such as an AIDS virus. Further, when the gelatin sponge is used as a temporary embolic material, it is required to be very finely cut into a thickness of about 1 mm before use in order to pass the gelatin sponge through a catheter, and a very high degree of proficiency of a doctor is required. There is also a problem that there is a great difference in remedy effects between individuals. Further, although crosslinked starch is also generally used as the temporary embolic material, it is decomposed in minutes by amylase in the blood; therefore, it was not an embolic material that is effective for a comparatively long fixed period such as one week to 3 months.

Japanese Patent Unexamined Publication No. 2004-167229 discloses a blood vessel embolic material comprising a substantially granular particle having a water-swelling rate of at least 30% and degradability in phosphate buffered saline. However, the blood vessel embolic material is obtained by making a water-soluble polymer insoluble in water by methods such as block copolymerization by a biodegradable component, crosslinking and degradation, and since its degradation is caused by biodegradation, the control of the embolization time in the blood vessel was still inadequate.

DISCLOSURE OF INVENTION

It is an object to provide a blood vessel embolic material temporarily embolizing a blood vessel in a living body and superior in a catheter passing property and the controllability of an embolization time.

Namely, the present invention relates to a pearl shape polyvinyl alcohol particle for a temporary embolic material, wherein a degree of hydrolysis is at least 90% by mol and an average particle diameter is 70 μm to 1000 μm.

An average degree of polymerization of polyvinyl alcohol is preferably 80 to 600 and more preferably 80 to 350.

The polyvinyl alcohol particle of the present invention is preferably obtained by dispersing a polyvinyl ester solution (b) in which an alcohol or an alcohol and methyl acetate (a) is used as a solvent, in a medium (c) that is not substantially compatible with either of polyvinyl ester, a hydrolyzed product of the ester and the component (a) and is more viscous than the component (b), as a particle and s hydrolyzing the dispersion in the presence of a hydrolytic catalyst.

A weight ratio of the polyvinyl ester solution (b)/the medium (c) is preferably 2/8 to 6/4 and more preferably 4/6 to 5/5.

Further, the present invention relates to a temporary embolic material dispersing the polyvinyl alcohol particle in a contrast agent and a temporary embolic material dissolving the polyvinyl alcohol particle in a contrast agent.

Further, the present invention relates to a temporary embolic material in which the polyvinyl alcohol particle is further dispersed in the temporary embolic material dissolving the polyvinyl alcohol particle in a contrast agent.

BEST MODE FOR CARRYING OUT THE INVENTION

The particle of the present invention is a particle for a temporary embolic material, and is a pearl shape polyvinyl alcohol (PVA) particle wherein a degree of hydrolysis is at least 90% by mol and an average particle diameter is 70 μm to 1000 μm. Herein, the pearl shape is not a granular shape or an atypical powder article but represents a particle having a fixed spherical degree.

The degree of hydrolysis of the PVA particle of the present invention is preferably at least 90% by mol, more preferably 94 to 99% by mol and further preferably 95 to 98.9% by mol. When the degree of hydrolysis is less than 90% by mol, the particle is easily swollen by a contrast agent; therefore, passing property in a catheter is bad and it is not preferable because sticking is provoked or pressure at injecting the embolic material of the present invention through the catheter is very high leading to remarkably lower manipulativity.

The average particle diameter of the PVA particle is preferably 70 μm to 1000 μm, more preferably 100 μm to 300 μm and further preferably 100 μm to 220 μm. Further, the PVA particle in which the content of a particle that is at least 1200

μm is at most 3% by weight. When the average particle diameter of the PVA particle is less than 70 μm, it is not preferable because a site other than the objective blood vessel tends to be embolized. Further, when it is larger than 1000 μm, the passing property in a catheter of the particle tends to be remarkably lowered depending on the kind of the catheter used or injection of the particles tends to be impossible. Further, the average particle diameter is a value in a state in which a fixed amount of PVA is dispersed in isopropyl alcohol, unless otherwise noticed in the present specification.

An average degree of polymerization of the PVA particle is preferably 80 to 600, more preferably 80 to 350 and further preferably 100 to 220. When the average degree of polymerization of the PVA particle is less than 80, it is not a range of degree of polymerization at which the particle can be industrially produced stably, and it is not preferable because the embolization time tends to be extremely shortened. When the average degree of polymerization is more than 600, the dissolution time of the particle in the blood vessel is largely elongated and since the particle remains in the body, functions as the temporary embolic material are lowered. The temporary embolic material in the present invention is an embolic material in which the embolization time of the blood vessel is about 30 minutes to 3 months.

The PVA particle of the present invention can be produced, for example, in accordance with the production process of granular polyvinyl alcohol described in Japanese Patent Unexamined Publication No. 56-120707. Specifically, the PVA particle can be produced by dispersing a polyvinyl ester solution (b) including an alcohol or an alcohol and methyl acetate as solvent (a), in a medium (c) that is not substantially compatible with either of polyvinyl ester, a hydrolyzed product of the ester and the solvent (a) and is more viscous than the solution (b), as a particle and hydrolyzing the dispersion in the presence of a hydrolytic catalyst.

The polyvinyl ester includes homo polymers and copolymers of vinyl esters such as vinyl acetate, vinyl propionate, vinyl formate, vinyl stearate and vinyl benzoate. Further, as the polyvinyl ester in the present invention, there can also be mentioned copolymers with monomers copolymerizable with vinyl ester, for example, unsaturated carboxylic acids such as unsaturated acids such as acrylic acid, methacrylic acid, crotonic acid, maleic acid, maleic anhydride and itaconic acid, or salts thereof, or mono- or dialkyl esters thereof; various α-olefins such as ethylene and propylene; alicyclic hydrocarbons such as norbornane; nitriles such as acrylonitrile and methacrylonitrile; amides such as diacetone acrylamide, acrylamide and methacrylamide; olefin sulfonic acids such as ethylene sulfonic acid, allyl sulfonic acid and methallyl sulfonic acid or salts thereof; alkyl vinyl ethers; dimethylallyl vinyl ketone, N-vinyl pyrrolidone, (meth)acrylate, further, monomers containing a cationic group such as N-acrylamidemethyltrimethylammonium chloride, N-acrylamideethyltrimethylammonium chloride, N-acrylamidepropyltrimethylammonium chloride, 2-acryloxyethyltrimethylammonium chloride, 2-methacryloxyethyltrimethylammonium chloride, 2-hydroxy-3-methacryloyloxypropyltrimethylammonium chloride, allyltrimethylammonium chloride, methallyltrimethylammonium chloride, 3-butenetrimethylammonium chloride, dimethyldiallyammonium chloride and diethyldiallylammonium chloride; monomers containing an acetoacetyl group; allyl sulfonic acid, 2-acrylamide-2-methylpropene sulfonic acid, 3,4-diacetoxy-1-butene, glycerin monoallyl ether, isopropenyl acetate, 1-methoxyvinyl acetate and 1,4-diacetoxy-2-butene.

As the alcohol in the alcohol or the alcohol and methyl acetate as solvent (a), lower aliphatic alcohols such as methanol, ethanol, isopropyl alcohol and propyl alcohol can be used. These alcohols can be used alone or a mixture of at least 2 kinds can be used in an arbitrary proportion. Among these, methanol, ethanol and isopropyl alcohol are preferably used from the viewpoint of obtaining the control of the particle diameter in the hydrolysis reaction and a practically usable speed of the hydrolysis degree. When an alcohol and methyl acetate are used in combination, the proportion of alcohol/methyl acetate is preferably at least 0.5 by weight ratio and more preferably at least 1.5 from the viewpoint of hydrolytic efficiency. Further, various organic solvents having further lower polarity than methyl acetate can also be used in combination.

The content of polyvinyl ester in the polyvinyl ester solution (b) is not specifically limited, but usually 10 to 80% by weight based on the total solvent. The polyvinyl ester solution (b) may contain 0.05 to 10% by weight of water based on polyvinyl ester and can play roles of making random the distribution of a residual acetic acid group in a hydrolyzed article and controlling the degree of hydrolysis by the presence of a small amount of water.

The medium (c) is not substantially compatible with either of polyvinyl ester used, the hydrolyzed product of the ester and solvent (a) including an alcohol or an alcohol and methyl acetate, and is more viscous than the polyvinyl ester solution (b), and examples thereof include aliphatic saturated hydrocarbons such as liquid paraffin and kerosene, aromatic hydrocarbons and alicyclic hydrocarbons. These can be used alone or a mixture of at least 2 can be used. Among these, liquid paraffin is preferable because the polyvinyl ester solution can be homogeneously dispersed.

The viscosity of the medium (c) is not specifically limited so far as it is higher than the viscosity of the polyvinyl ester solution (b).

The proportion of the polyvinyl ester solution (b) and the medium (c) used is preferably 2/8 to 6/4 by a weight ratio and more preferably 4/6 to 5/5. When the proportion of the polyvinyl ester solution (b) used is less than 20% by weight, it is not preferable because production efficiency is lowered. When the proportion of the polyvinyl ester solution (b) used exceeds 60% by weight, dispersibility is deteriorated, an agglomerate of a lot of particles is easily formed and the average particle diameter of the pearl shape PVA particle tends to be enlarged.

As the hydrolytic catalyst, a usual alkali catalyst that is used for hydrolyzing polyvinyl ester to produce PVA can be used. The amount of the hydrolytic catalyst used is suitably determined depending on the concentration of polyvinyl ester and the objective degree of hydrolysis, but is usually a proportion of 0.1 to 30 mmol based on the vinyl acetate unit (1 mole) in polyvinyl ester and preferably 2 to 17 mmol.

The reaction temperature of the hydrolysis reaction is preferably 20° C. to 60° C. When the reaction temperature is at most 20° C., the reaction speed is lessened and the reaction efficiency is lowered. When it exceeds 60° C., it is at least the boiling point of the solvent and not preferable from the viewpoint of safety.

The PVA particle having the high degree of hydrolysis of the present invention is preferably produced by a two-stage hydrolysis because of the purpose of safety such as the properties of the PVA particle obtained and reduction of toxicity to the human body due to liquid paraffin taken in the inside of the PVA particle. In primary hydrolysis, after the hydrolysis is carried out until the degree of hydrolysis is 75 to 90% by mol, the particle is separated from the reaction slurry by a solid liquid separator such as a centrifugal separator or by filtration with an Advantec filter paper No. 2 or No. 63 in an experiment room and rinsing is carried out with an appropriate solvent such as methanol, methyl acetate, ethyl acetate or a mixture of methyl acetate/methanol if necessary, to obtain a primarily hydrolyzed particle. Successively, the obtained primarily hydrolyzed particle is dispersed in an alcohol solvent such as methanol or ethanol and the homestretch of the hydrolysis is carried out. When the desired degree of hydrolysis is attained, the reaction is terminated and the PVA particle (secondarily hydrolyzed particle) of the present invention is obtained by a method similar to the collection of the particle in the primary hydrolysis. Then, rinsing is carried out with saline if necessary.

As a sterilization method of uncrosslinked PVA at preparation of the PVA, there are used γ-rays, pressured vapor sterilization, a method of immersing in Hibitane solution (chlorhexidine gluconate solution SUMITOMO SEIYAKU CO., JAPAN) and a method of rinsing with sterile saline.

For the average particle diameter of PVA, the pearl shape PVA particle with an arbitrary particle diameter can be adjusted by carrying out the physical sieving of the pearl shape PVA particle obtained in the production method with a standard mesh if necessary. Further, in order to lessen the average particle diameter to a desired level, the particle diameter can be controlled by enhancing a stirring speed in the hydrolysis, setting the viscosity of the medium (c) such as liquid paraffin higher than the viscosity of the polyvinyl ester solution (b) or controlling the ratio of the medium (c) to the polyvinyl ester solution (b), in accordance with the production process of granular polyvinyl alcohol described in Japanese Patent Unexamined Publication No. 56-120707.

For example, when the particle diameter is set in the range of 105 to 177 μm, those with a particle diameter sieved by 145 meshes (105 μm) ON and 80 meshes (177 μm) PASS are used. Further, when it is set at 177 to 297 μm, those with a particle diameter sieved by 80 meshes (177 μm) ON and 48 meshes (297 μm) PASS may be used. When it is set at 297 to 500 μm, those with a particle diameter sieved by 48 meshes (297 μm) ON and 32 meshes (500 μm) PASS may be used.

Further, as the specific method of obtaining the pearl shape PVA particle with a desired average particle diameter according to the above-mentioned hydrolysis condition, for example, the hydrolysis may be carried out by setting the concentration of the methanol solution (b) at 40% in the case of polyvinyl ester with the average degree of polymerization of 500, and setting the concentration of the methanol solution (b) at 50% in the case of polyvinyl ester with the average degree of polymerization of 150 to 200 and setting the proportion of the solution (b) to the medium (c) such as liquid paraffin at 50/50 in a weight ratio, in order to obtain the pearl shape PVA particle with an average particle diameter of about 150 μm. Further, in order to set the average particle diameter at about 500 μm, the viscosity of the polyvinyl ester solution (b) may be set at a higher value than that of the medium (c) (for example, the resin content of the polyvinyl acetate solution with the degree of polymerization of 500 is set at 50%).

Further, the average particle diameter of each pearl shape PVA particle can be determined by dispersing each PVA particle in isopropyl alcohol (IPA) and measuring an average cord length (μm) with Lasentec M100 (an inline type particle monitoring system, manufactured by Mettler-Toledo Auto Chem, Columbia, USA). Specifically, a range of 0.8 to 1000 μm is divided into the cord length with 38 channels, the particle numbers of each channel is counted and it is determined by the formula below.

$$\text{Average cord length} = \Sigma(Yi \times Mi^2)/\Sigma Yi$$

Yi: The count number of particle monitored by the Lasentec M100
Mi: The cord length of each channel The present invention relates to a temporary embolic material (i) dispersing the obtained PVA particle in a contrast agent.

As the contrast agent, either of an ionic contrast agent and a non-ionic contrast agent can be used. Specifically, there are mentioned IOPAMIRON (manufactured by Schering AG), OYPALOMIN (manufactured by Fuji Pharma Co., Ltd.), HEXABRIX (manufactured by Terumo Corporation), OMNIPAQUE (manufactured by Daiichi Seiyaku Co., Ltd.), UROGRAFIN (manufactured by Schering AG) and IOMERON (manufactured by Eisai Co., Ltd.).

The PVA particle is preferably used at a proportion of at most 20% by weight based on the contrast agent from the viewpoint of necessity to secure permeability in a catheter. In this case, after the PVA particle is dispersed in the contrast agent, it is preferably used as a temporary embolic material after leaving it at rest for 5 to 15 minutes. Time till re-open after embolization is controlled by the degree of polymerization of PVA, the degree of hydrolysis and the time for leaving in the contrast agent. The embolization time can be elongated by heightening the degree of polymerization and the degree of hydrolysis of PVA. Further, when the preliminary time for leaving in the contrast agent is long, the embolization time becomes short. The preliminary time for leaving in the contrast agent affects most greatly for controlling the embolization time. When the time for leaving is less than 5 minutes, the swelling of the PVA particle by the contrast agent is inadequate and the time until the re-dissolution of the PVA particle after embolization in the blood vessel tends to be elongated. When it exceeds 15 minutes, inversely, the PVA particle is easily in a state of coagulation because the PVA particle is presumably swollen by the contrast agent too much; therefore permeability in a catheter is lowered and the manipulativity of the embolization remedy tends to be remarkably lowered.

Further, the present invention relates to a temporary embolic material (ii) dissolving the PVA particle in a contrast agent. Specifically, it is a paste temporary embolic material obtained by adding the PVA particle by at most 20% by weight based on 100 parts by weight of the contrast agent, heating them at about 50° C. to 70° C. and dissolving them for about 30 minutes to 1 hour.

Further, the present invention relates to a temporary embolic material (iii) dispersing the PVA particle in the paste temporary embolic material. The embolic material (iii) can control the embolization time by changing the mixing weight ratio of the PVA (A) dissolved in the paste temporary embolic material and the PVA particle (B) in a dispersion state. When the proportion of the PVA (A) dissolved is too small in the mixing, the embolization time in the blood vessel is occasionally too long at embolization in the blood vessel depending on the diameter of the blood vessel and when it is too large, the embolization time tends to be too short (for example, about 15 minutes), and the objective embolization remedy may not be carried out.

The temporary embolic materials (i) to (iii) can be used by selection in accordance with the objective embolization time. Although it is slightly fluctuated depending on the degree of hydrolysis, each of the embolic materials has the embolization time controlled as below respectively.

The temporary embolic material (i): About 3 months
The temporary embolic material (ii): About 2 hours
The temporary embolic material (iii)
- (A)/(B)=9/1 (weight ratio): About 5 hours
- (A)/(B)=5/5 (weight ratio): About 24 hours
- (A)/(B)=3/7 (weight ratio): About 1 month Therapeutic medicine may be mixed in the temporary embolic material of the present invention. The therapeutic medicine can be compounded in the temporary embolic material by a method of carrying and supporting them on the pearl shape PVA particle at the time of mixing the contrast agent with the PVA particle or in a solvent dissolving the therapeutic medicine. The therapeutic medicine include anticancer agents such as SMANCS and cyclophosphamide, steroid hormone agents, drugs used for liver disorders, drugs used for diabetes mellitus, antioxidants, peptide drugs, molecular targeted therapeutic drugs and chemotherapeutic agents, and antibiotics. Further, there are mentioned a basic fibroblast growth factor (bFGF) being a cell growth factor, a platelet-derived growth factor (PGF), a transforming growth factor β1 (TGF-(β1) and a vascular endothelial cell growth factor (VEGF).

A catheter used for delivering the temporary embolic material of the present invention into the blood is not specifically limited and a catheter, TRANSIT manufactured by CORDIS Inc. and a catheter, PROGREAT manufactured by Terumo Corporation can be suitably selected.

EXAMPLES

The PVA particle of the present invention, the production process of the particle and the temporary embolic material of the present invention are illustrated further in detail based on Examples, but the present invention is not limited to only such Examples. Further, "parts" below mean "parts by weight" unless otherwise noticed.

Example 1

Production of PVA Particle 1

Average Particle Diameter of 150 μm, Degree of Hydrolysis of 98.2% by Mol, Pearl Hydrolyzed Product with Average Degree of Polymerization of 150

Methanol was added to a 55% methanol solution of polyvinyl acetate with an average degree of polymerization of 155 (water content of 0.05%) to dilute it to a resin content of 50%. 100 Parts of the solution was charged in a reaction can equipped with a stirrer and a 2% methanol solution that is converted to the content of Na of NaOH as a hydrolytic catalyst was added at a proportion of 3 mmol for the vinyl acetate unit of polyvinyl acetate while stirring by keeping the temperature at 25° C. Successively, 100 parts of liquid paraffin was added thereto and when the stirring speed was adjusted to 250 rpm, polyvinyl acetate was dispersed in liquid paraffin in a spherical shape. The reaction was carried out while keeping temperature at 25° C., the reaction was terminated after the lapse of time of 60 minutes and the PVA particle was separated by carrying out solid liquid separation by a centrifugal separator. The particle was rinsed by an extraction method using an ethyl acetate solution at a temperature of 50° C. and then dried by hot wind at a temperature of 80° C. for 2 hours. 100 Parts of the PVA particle obtained (primarily hydrolyzed particle) was dispersed again in 600 parts of a methanol solution, 20 parts of a hydrolytic catalyst (2% NaOH/methanol solution that is converted to the weight of Na), the secondary hydrolysis was carried out over 1 hour at a temperature of 50° C., the PVA particle was separated again by a centrifugal separator, the particle was rinsed by an extraction method using an ethyl acetate solution at a temperature of 50° C. and then dried by hot wind at a temperature of 80° C. for 2 hours to obtain a PVA particle 1 with an average degree of polymerization of 150.

(Degree of Hydrolysis)

The degree of hydrolysis of the PVA particle was measured according to JIS K-6726 and determined as 98.2% by mol.

(Average Particle Diameter)

The average particle diameter of the PVA particle was measured by adding 10 parts of the PVA particle in 100 parts of isopropyl alcohol being a poor solvent for the highly hydrolyzed PVA and setting the particle diameter as a cord length under stirring using Lasentec M100. The average particle diameter of the PVA particle was 150 μm.

Example 2

Production of PVA Particle 2

Average Particle Diameter of 152 μm, Degree of Hydrolysis of 97.5% by Mol, Pearl Hydrolyzed Product with Average Degree of Polymerization of 200

A PVA particle was obtained in a similar manner as Example 1 except that a 55% methanol solution of polyvinyl acetate with an average degree of polymerization of 205 was used and the reaction time at the secondary hydrolysis was set at 40 minutes. The PVA particle 2 obtained had an average particle diameter of 152 μm, a degree of hydrolysis of 97.5% by mol and an average degree of polymerization of 200.

Example 3

Production of PVA Particle 3

Average Particle Diameter of 154 μm, Degree of Hydrolysis of 95% by Mol, Pearl Hydrolyzed Product with Average Degree of Polymerization of 150

A PVA particle was obtained in a similar manner as Example 1 except that the reaction time at the secondary hydrolysis was set at 35 minutes. The PVA particle 3 obtained had a particle diameter of 154 inn, a degree of hydrolysis of 95% by mol and an average degree of polymerization of 150.

Example 4

Production of PVA Particle 4

Average Particle Diameter of 156 μm, Degree of Hydrolysis of 99.2% by Mol, Pearl Hydrolyzed Product with Average Degree of Polymerization of 300

A PVA particle was obtained in a similar manner as Example 1 except that polyvinyl acetate with an average degree of polymerization of 300 was used. The PVA particle 4 obtained had a particle diameter of 156 μm, a degree of hydrolysis of 99.2% by mol and an average degree of polymerization of 300.

Example 5

Production of PVA Particle 5

Average Particle Diameter of 152 μm, Degree of Hydrolysis of 97.0% by Mol, Pearl Hydrolyzed Product with Average Degree of Polymerization of 300

A PVA particle was obtained in a similar manner as Example 1 except that polyvinyl acetate with an average degree of polymerization of 300 was used and the reaction time at the secondary hydrolysis was set at 30 minutes. The PVA particle 5 obtained had a particle diameter of 152 μm, a degree of hydrolysis of 97.0% by mol and an average degree of polymerization of 300.

Example 6

Temporary Embolic Material 1

20 Parts of the PVA particle obtained in Example 1 was dispersed for 100 parts of a contrast agent (OYPALOMIN 300, manufactured by Fuji Pharma Co., Ltd.) and the mixture was left at rest for 5 to 15 minutes to prepare an embolic material 1.

Example 7

Temporary Embolic Material 2

20 Parts of the PVA particle obtained in Example 2 was dissolved for 100 parts of a contrast agent (OYPALOMIN 300) at a temperature of 60° C. over 45 minutes to prepare a pasty embolic material 2.

Example 8

Temporary Embolic Material 3

20 Parts of the PVA particle obtained in Example 1 was dissolved at 60° C. over 60 minutes for 100 parts of a contrast agent (OYPALOMIN 300) to prepare a pasty embolic material. Then, 10 parts of the dispersion of the contrast agent obtained by dispersing 20 parts of the PVA particle obtained in Example 3 in 100 parts of the contrast agent (OYPALOMIN 300) was mixed with 90 parts of the pasty embolic material and a temporary embolic material 3 was obtained so that the weight ratio (A)/(B) of PVA (A) in a dissolved state to a PVA particle (B) being in a dispersion state was 9/1.

Example 9

Temporary Embolic Material 4

A temporary embolic material 4 was obtained in a similar manner as Example 8 except that the amount of the pasty embolic material was changed to 50 parts, the amount of the dispersion of the contrast agent of the PVA particle 3 was changed to 50 parts and the weight ratio of (A)/(B) was 5/5 in Example 8.

Example 10

Temporary Embolic Material 5

A temporary embolic material 5 was obtained in a similar manner as Example 8 except that the amount of the pasty embolic material was changed to 30 parts, the amount of the dispersion of the contrast agent of the PVA particle 3 was changed to 70 parts and the weight ratio of (A)/(B) was 3/7 in Example 8.

Example 11

Temporary Embolic Material 6

20 Parts of the PVA particle obtained in Example 4 was dispersed for 100 parts of a contrast agent (OYPALOMIN 300) and after leaving the mixture at rest for 15 minutes, it was used as a temporary embolic material 6.

Example 12

Temporary Embolic Material 7

20 Parts of the PVA particle obtained in Example 5 was dispersed for 100 parts of a contrast agent (OYPALOMIN 300) and after leaving the mixture at rest for 15 minutes, it was used as a temporary embolic material 7.

The temporary embolic materials 1 to 7 obtained were evaluated by the evaluation methods below.

(Catheter Passing Test)

1 G of each of the temporary embolic materials 1 to 5 was dispersed in 5 ml of a contrast agent (OYPALOMIN 300) to prepare spherical particle dispersions. Each of the spherical particle dispersions and the temporary embolic materials 6 and 7 was injected in 2.7 Fr micro catheter (PROGREAT MC-PC2710, manufactured by Terumo Corporation) for hepatic artery embolization from a 2.5 cc injection syringe, and the presence or absence of inhalation resistance and a sticking phenomenon was confirmed. Further, after injecting a small amount of saline, the catheter was incised in a longitudinal direction, the inside of the catheter was visually observed and the presence or absence of the residual spherical particle was observed.

The flow rates of the temporary embolic materials 1 to 7 (spherical particle dispersions) were not changed and the catheter passing property was good. Further, when the inside of the catheter was visually observed, no residual spherical particle was observed at all.

(Evaluation of opening time of renal artery embolization in animal experiment)

The temporary embolic materials 1 to 6 obtained in Examples 6 to 11 were injected in the renal artery of anesthetized pigs using micro catheters (PROGREAT MC-PC2710, catheters manufactured by Terumo Corporation). The observation of the embolization situation of the blood vessel was successively carried out by X-ray photography of the kidneys in the cases that the embolization time was estimated to be at most about 25 hours, the kidneys of pigs were extirpated when the revascularization of the embolized artery on a X-ray photograph was recognized, and the tissue segments of vascular embolized sites were prepared to observe the situation of vascular embolization and the influence on peripheral tissues. With respect to those in one month to several months units, confirmation of the revascularization time was carried out through observation of the appearance by X-ray photography at every constant period.

The time starting revascularization was as follow.

| | |
|---|---|
| The temporary embolic material 1 | About 3 months |
| The temporary embolic material 2 | About 2 hours |
| The temporary embolic material 3 | About 5 hours |
| The temporary embolic material 4 | About 24 hours |
| The temporary embolic material 5 | About 1 month |
| The temporary embolic material 6 | About 3 weeks |

Further, it was confirmed by observation after the revascularization that the embolized blood vessel was open without provoking embolization by redistribution to the peripheral vessels.

Minimization of the blood vessel diameter and regression of the vascular network were confirmed in the blood vessel at the embolized site and when this was used for embolization of the malignant tumor nutrition blood vessel, a result of expecting effectiveness in cancer treatment was obtained.

(Evaluation of opening time of pulmonary artery embolization in animal experiment)

When a ballooncatheter was inserted in the pulmonary artery segmental branch of a pig under general anesthesia and the temporary embolic material 7 obtained in Example 12 was injected by hand pressure while confirming a fluoroscopic image, the blood flow of the segmental branch was stopped when 5 ml of the agent was injected. Then, the partial recovery of the blood flow was confirmed after 15 minutes from the embolization and the blood flow on the angiographic photograph was nearly recovered to the pre-embolized state after 30 minutes.

(Dissolution Property in Human Fresh Frozen Plasma)

The change of average particle diameters in the PVA particle or the contrast agent of the temporary embolic material and human B-type fresh frozen plasma (FFP) was measured by a dissolution test measuring device, Lasentec M100. The measurement procedure is as below.

1. Constant-temperature water at 37° C. is preliminarily flown in a jacket portion of a 400 ml separable flask equipped with a jacket (hereinafter, a flask).
2. 150 Ml of FFP is preliminarily unfrozen with constant-temperature water at 37° C.
3. Into the flask, 10 parts of the PVA particle or the contrast agent of the temporary embolic material 1 g/5 ml (IOMERON 300, manufactured by Eisai Co., Ltd.) is charged, successively, 300 parts of FFP is charged in the flask and measurement by the Lasentec is started while stirring the mixture with a paddle at 150 rpm.

Stirring and measurement were carried out at 37° C. and the time at which the particle was not counted by Lasentec was set as dissolution. The result is shown below.

| | |
|---|---|
| The PVA particle 1 | Dissolved after 3 hours |
| The PVA particle 2 | Dissolved after 5 minutes |
| The temporary embolic material 1 | Dissolved after 25 minutes |
| The temporary embolic material 2 | Dissolved after 45 minutes |
| The temporary embolic material 3 | Dissolved after 1 hour |

INDUSTRIAL APPLICABILITY

According to the present invention, a particle for a temporary blood vessel-embolic agent that does not provoke sticking, is good in permeability in a catheter and can control an embolization time, and an embolic agent can be provided. The embolic agent is naturally discharged out of the body after absorption in the living body. Further, since it is not a temporary embolic agent derived from the blood, there is no fear of the diffusion of blood mediated infections such as AIDS and Bovine Spongiform Encephalopathy. Further, a fear of provoking agglomeration blocking in the blood vessel other than the objective one is little.

The invention claimed is:

1. A pearl shape polyvinyl alcohol particle for use as a temporary embolic material, wherein a degree of hydrolysis is 95 to 98.9% by mol, an average degree of polymerization of polyvinyl alcohol is 80 to 350 and an average particle diameter is 100 μm to 220 μm.

2. A process for producing the particle of claim 1, comprising the steps of:
dissolving polyvinyl ester in solvent (a) to make solution (b), wherein solvent (a) is an alcohol or is an alcohol and methyl acetate,
dispersing solution (b) in a medium (c), wherein the dispersing step forms a particle, and wherein medium (c) is not substantially compatible with each of the polyvinyl ester, the solvent (a), and a hydrolyzed product of the ester, and wherein the medium (c) is more viscous than the solution (b),
and hydrolyzing solution (b) in the presence of a hydrolytic catalyst.

3. The production process of claim 2, wherein a weight ratio of the polyvinyl ester solution (b)/the medium (c) is 2/8 to 6/4.

4. The production process of claim 2, wherein a weight ratio of the polyvinyl ester solution (b)/the medium (c) is 4/6 to 5/5.

5. A temporary embolic material comprising the particle of claim 1 and a contrast agent, wherein the particle is dispersed in the contrast agent.

6. A temporary embolic material comprising the particle of claim 1 and a contrast agent, wherein the particle is dissolved in the contrast agent.

7. A temporary embolic material comprising the particle of claim 1, and further comprising an additional pearl shape polyvinyl alcohol particle for use as a temporary embolic material, wherein in said additional particle a degree of hydrolysis is at least 90% by mol, an average degree of polymerization of polyvinyl alcohol is 80 to 350 and an average particle diameter is 100 μm to 220 μm, wherein the additional particle is dispersed in said temporary embolic material.

* * * * *